US011248634B2

(12) United States Patent
Shetty et al.

(10) Patent No.: US 11,248,634 B2
(45) Date of Patent: Feb. 15, 2022

(54) CLAMPING DEVICE

(71) Applicant: GE Precision Healthcare LLC, Milwaukee, WI (US)

(72) Inventors: Sudharshan M. Shetty, Bangalore (IN); Julien Marcotte, Saint-Vrain (FR); Hareesh Neeraje, Bangalore (IN); Vinay N., Bengaluru (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

(21) Appl. No.: 16/698,229

(22) Filed: Nov. 27, 2019

(65) Prior Publication Data

US 2021/0154074 A1    May 27, 2021

(51) Int. Cl.
*F16B 2/10* (2006.01)
*A61G 13/10* (2006.01)
*A61B 90/57* (2016.01)

(52) U.S. Cl.
CPC .............. *F16B 2/10* (2013.01); *A61G 13/101* (2013.01); *A61B 2090/571* (2016.02)

(58) Field of Classification Search
CPC ................... A61G 13/101; A61B 90/57; A61B 2090/571; F16B 2/10
USPC .............. 248/229.13, 229.23, 228.4, 231.51; 5/658, 503.1
See application file for complete search history.

(56) References Cited

U.S. PATENT DOCUMENTS

| 4,796,846 | A | * | 1/1989 | Meier | A61B 17/02 248/286.1 |
| 4,854,016 | A | * | 8/1989 | Rice | A61G 13/101 24/495 |
| 4,901,964 | A | * | 2/1990 | McConnell | A61G 13/101 24/514 |
| 5,135,210 | A | * | 8/1992 | Michelson | A61G 13/12 5/623 |
| 6,622,980 | B2 | | 9/2003 | Boucher et al. | |
| 6,663,055 | B2 | * | 12/2003 | Boucher | A61G 13/12 248/118 |
| 7,082,882 | B2 | * | 8/2006 | Heimbrock | A47B 23/025 108/152 |
| 7,520,007 | B2 | * | 4/2009 | Skripps | A61G 13/04 24/459 |

(Continued)

FOREIGN PATENT DOCUMENTS

| CN | 103037826 A | 4/2013 | |
| DE | 4309330 A1 * | 9/1994 | ............ F16L 3/1091 |

(Continued)

*Primary Examiner* — Jonathan Liu
*Assistant Examiner* — Guang H Guan
(74) *Attorney, Agent, or Firm* — McCoy Russell LLP

(57) ABSTRACT

A system with a clamping device attached to a clamping object is provided. One example clamping device includes a clamping jaw configured to pivot about a hinge and including a first clamping arm configured to interface with a first side of a clamping object and a body including a second clamping arm configured to interface with a second side of the clamping object, where the second side opposes the first side. The clamping device further includes a knob including a pin configured to axially translate toward and away from a third side of the clamping object, where the third side extends between the first side and the second side of the clamping object.

20 Claims, 5 Drawing Sheets

(56) References Cited

U.S. PATENT DOCUMENTS

| | | | |
|---|---|---|---|
| 8,302,228 B2* | 11/2012 | Aboujaoude | A61G 13/1245 |
| | | | 5/648 |
| 9,022,334 B1* | 5/2015 | DeMayo | F16M 13/022 |
| | | | 248/229.22 |
| 9,433,551 B2* | 9/2016 | Allen | A61G 13/10 |
| 9,469,438 B2* | 10/2016 | Nool | A61G 13/101 |
| 9,951,904 B2 | 4/2018 | Perez et al. | |
| 10,478,363 B2* | 11/2019 | Koch | F16M 13/022 |
| 10,478,364 B2* | 11/2019 | Fossez | A61G 13/1245 |
| 10,610,010 B2* | 4/2020 | Matlin | F16M 11/2092 |
| 10,952,914 B1* | 3/2021 | Miller | A61G 13/101 |
| 2005/0150044 A1 | 7/2005 | Votel | |
| 2008/0251672 A1 | 10/2008 | Barton et al. | |
| 2012/0126079 A1* | 5/2012 | Russell | A61G 13/101 |
| | | | 248/229.23 |
| 2016/0296401 A1* | 10/2016 | Cole | A61G 13/101 |
| 2017/0224569 A1* | 8/2017 | Pfeuffer | B25B 5/08 |
| 2021/0154074 A1* | 5/2021 | Shetty | F16B 2/10 |

FOREIGN PATENT DOCUMENTS

| | | |
|---|---|---|
| EP | 3085349 A1 | 10/2016 |
| WO | 2006085091 A1 | 8/2006 |

* cited by examiner

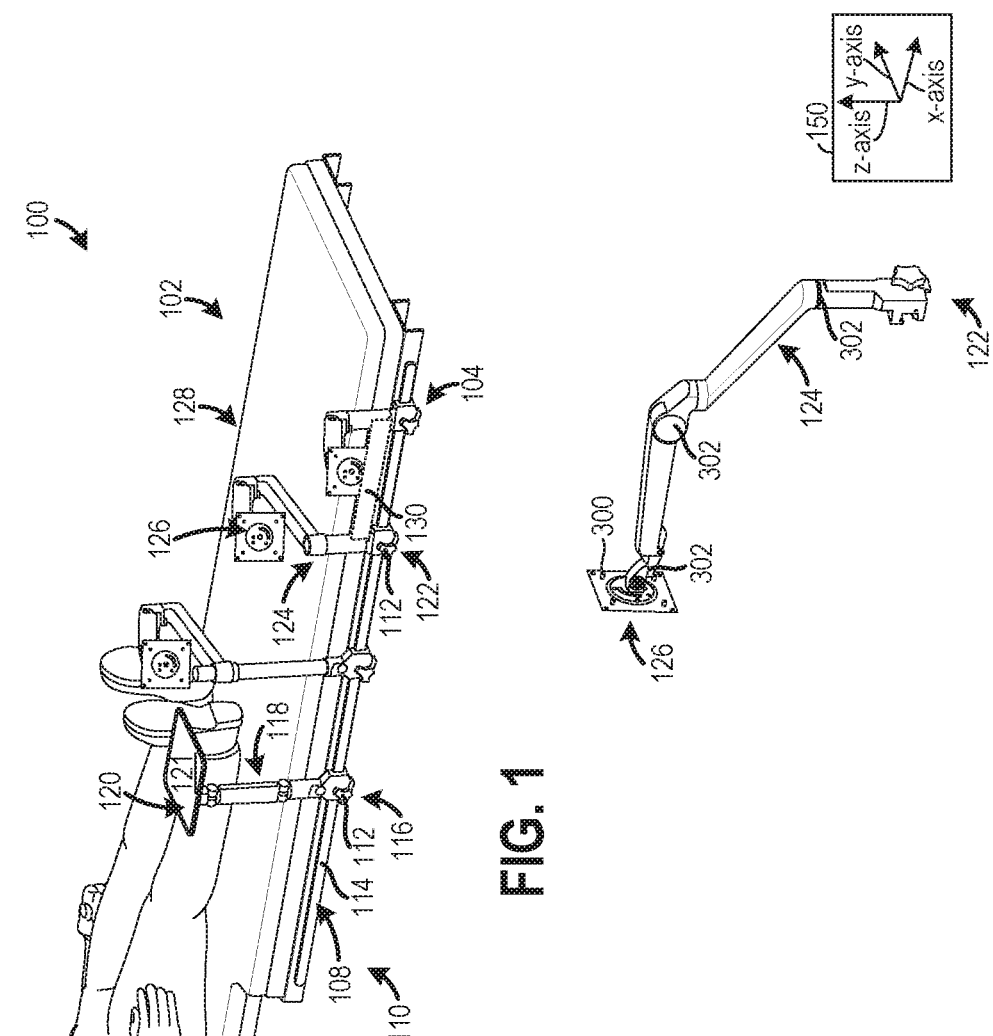
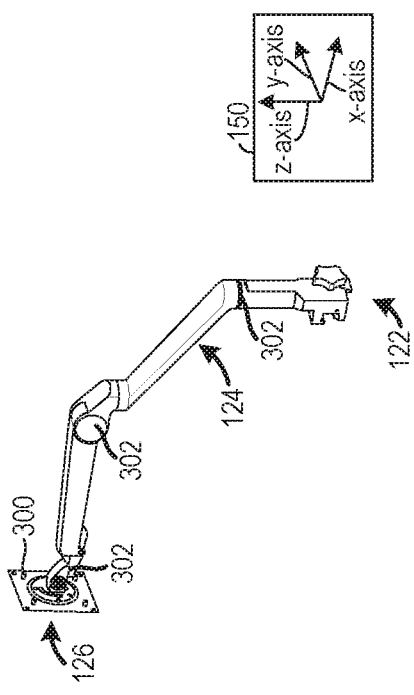
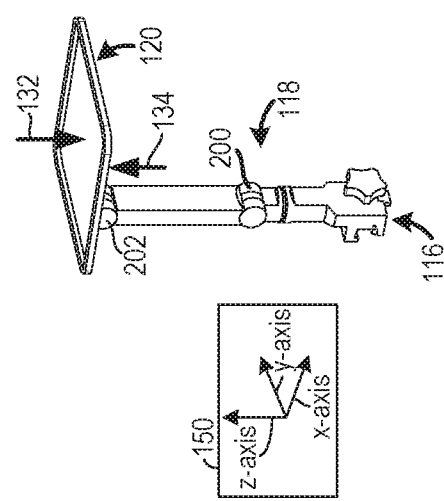

CLAMPING DEVICE

TECHNICAL FIELD

Embodiments of the subject matter disclosed herein relate to a clamping device.

BACKGROUND

Clamping devices are used in a wide variety of industries to removably attach one component to another. For instance, clamping devices have been employed in health care scenarios to clamp accessories and other components to tables, stretchers, beds, workstands, etc. Rails running down sides of a gurney may have clamps attached thereto, for example.

SUMMARY

In one embodiment, a clamping device is provided that includes a clamping jaw configured to pivot about a hinge and including a first clamping arm configured to interface with a first side of a clamping object, a body including a second clamping arm configured to interface with a second side of the clamping object, where the second side opposes the first side, and a knob including a pin configured to axially translate toward and away from a third side of the clamping object, where the third side extends between the first side and the second side of the clamping object.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 1 is a perspective view of a clamping object having a plurality of clamping devices attached thereto, according to an exemplary embodiment;

FIG. 2 is a detailed perspective view of one of the clamping devices, shown in FIG. 1;

FIG. 3 is a detailed perspective view of another one of the clamping devices, shown in FIG. 1;

FIGS. 1-12 are drawn approximately to scale. However, other relative dimensions may be used, in other embodiments.

DETAILED DESCRIPTION

The following description relates to various embodiments for a clamping device. The clamping device embodiments are described herein in the context of the health care industry. However, it will be appreciated that the clamping devices described herein have far-reaching applicability beyond the health care industry to, for example, manufacturing industries, the aerospace industry, the automotive industry, the office and home furnishing industry, etc.

Clamping device in-adjustability and dimensional variations in rails and other clamping objects can lead to clamping device incompatibility. Therefore, the clamping device embodiments described herein are highly adjustable and provide a robust interface between different objects when in an engaged configuration. Consequently, the devices can be used in a wide variety of situations where secure clamping is desired. To achieve the breadth of clamping compatibility, a rotatable clamping arm may be provided with a stationary clamping arm and a rotatable clamping arm configured to interface with opposing sides of an object when engaged, in one embodiment. Further in such an embodiment, a knob with an axially translatable pin is provided which interfaces with a lateral side of the object extending between the opposing sides. The axially translatable pin allows the device to be adjusted to accommodate for objects (e.g., rails) of varying thickness while also providing strong engagement between the device and rail with a reduced amount of play.

In one embodiment, the clamping device may include one or more removable spacers positioned between sections of a body of the device that includes the stationary clamping arm. The spacers enable additional dimensional adjustability to be achieved by the device. For instance, the number of spacers between the sections of the body may be increased to allow objects with greater heights to be clamped using the device. Conversely, the number of spacers between the body sections may be reduced to allow objects with smaller heights to be clamped by the device.

Figure 4:
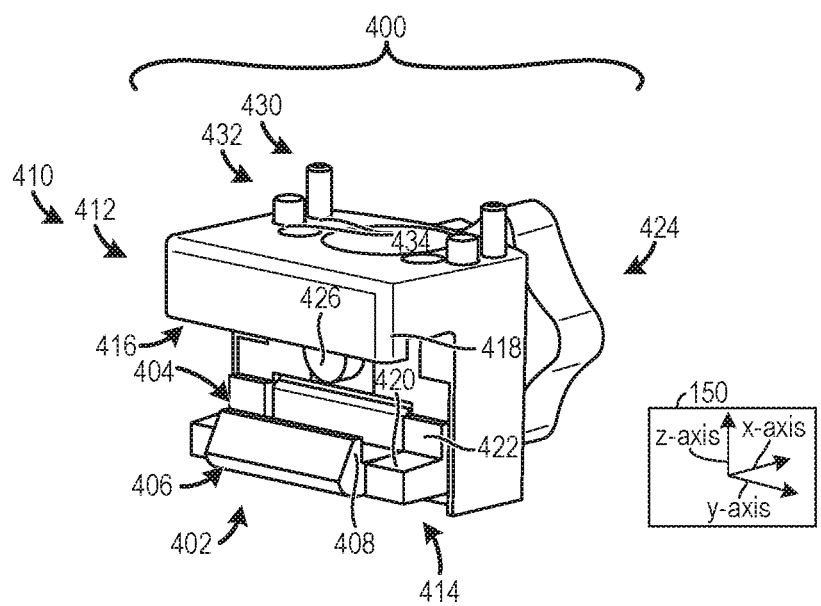
FIGS. 4-5 depict a clamping device in different height configurations, according to exemplary embodiments.
Figure 5:
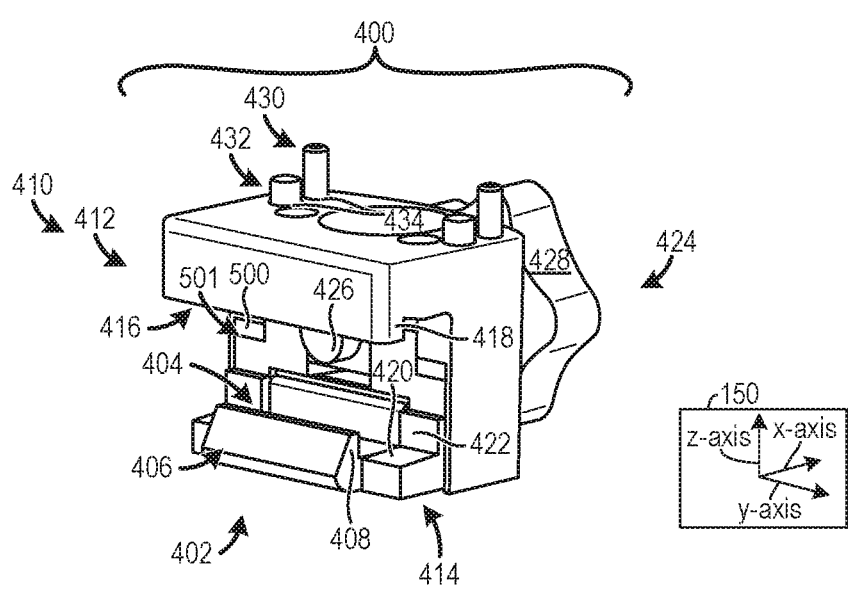
Figure 6:
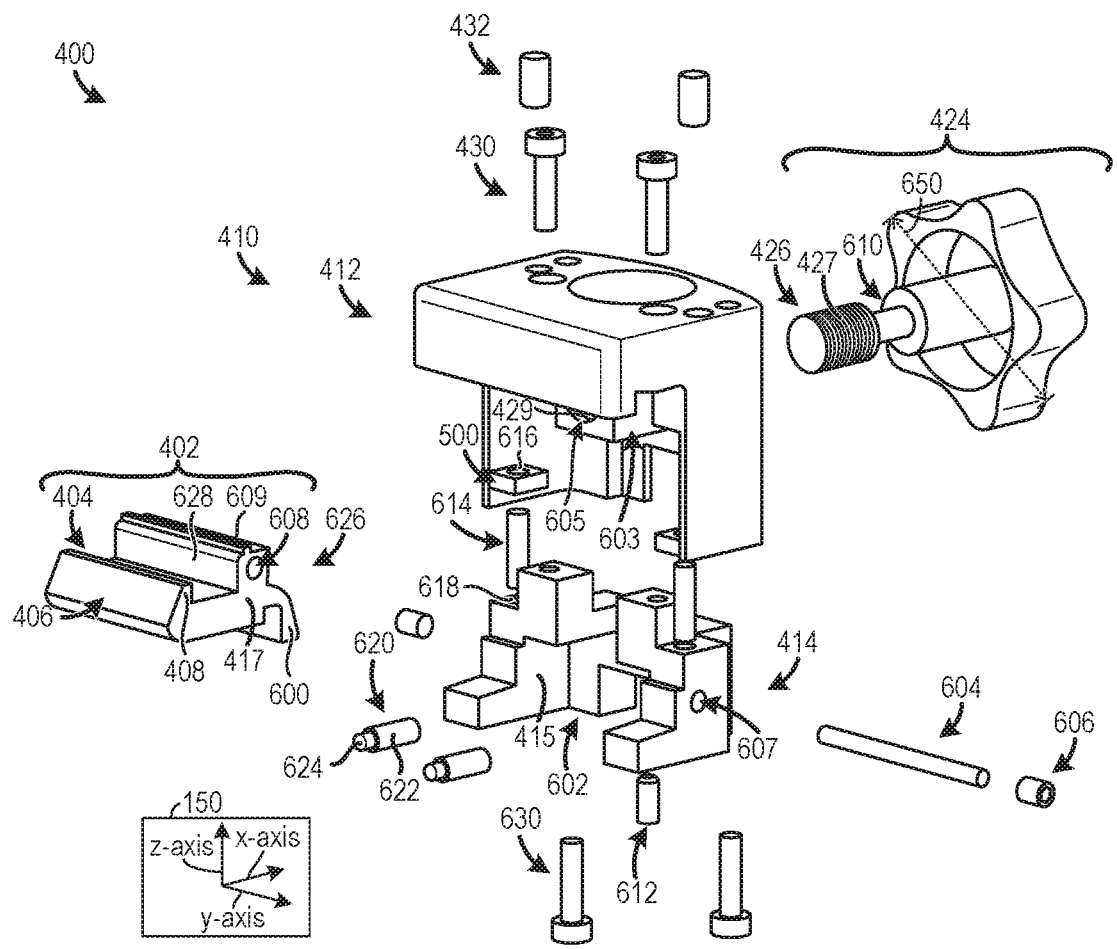
FIG. 6 is an exploded view of the clamping device, shown in FIG. 5, according to an exemplary embodiment.
Figure 7:
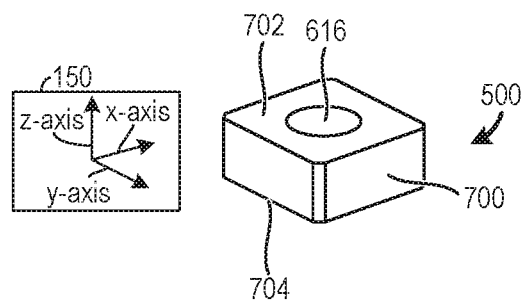
FIG. 7 is a detailed view of a spacer included in the clamping device, shown in FIG. 6, according to an exemplary embodiment.
Figure 8:
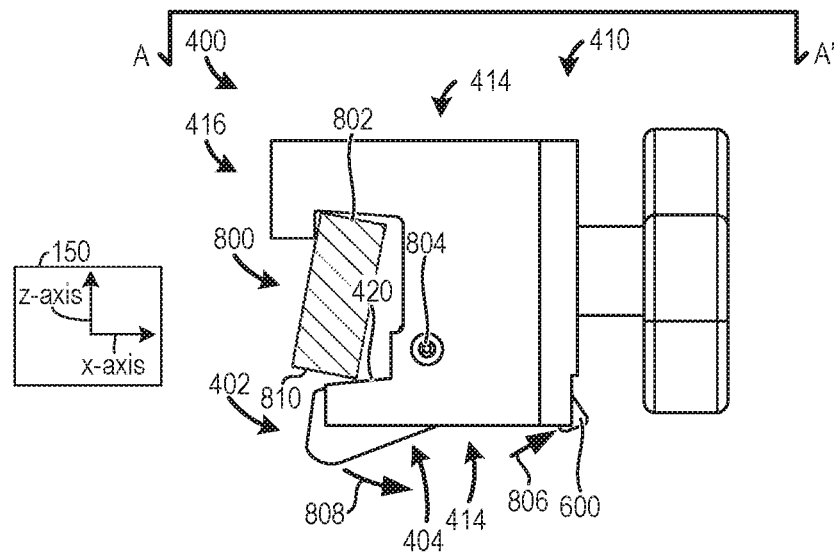
FIGS. 8-10 is a clamping sequence for the clamping device, shown in FIG. 5, according to an exemplary embodiment.
Figure 9:
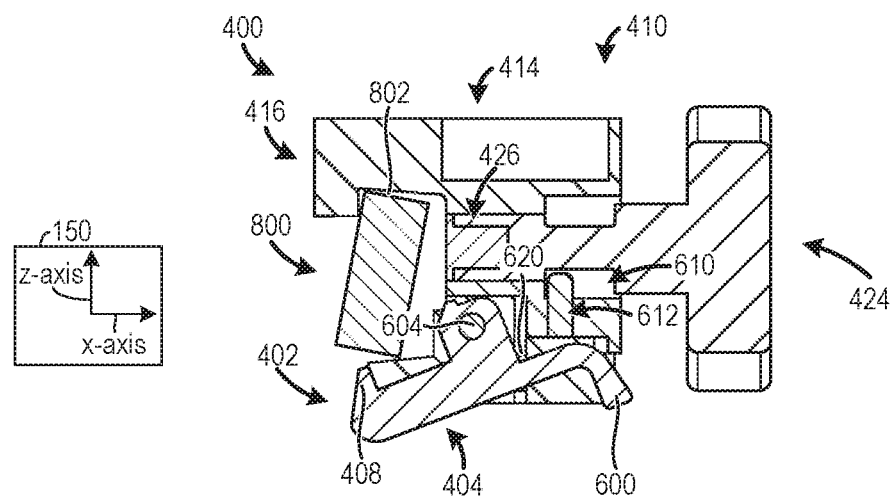
Figure 10:
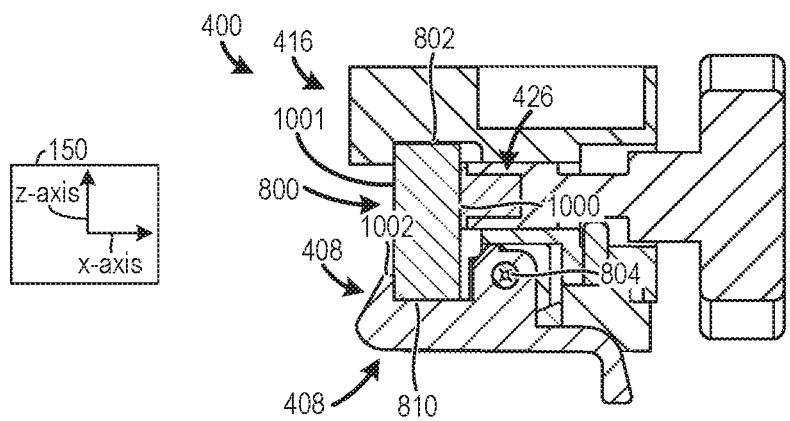
Figure 11:
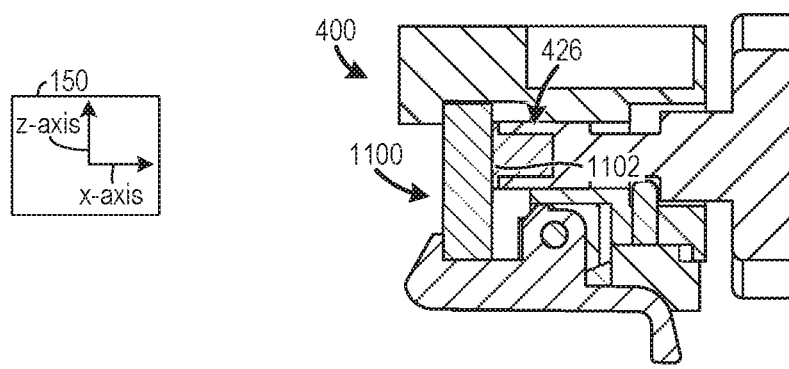
FIG. 11 is a cross-sectional view of the clamping device, shown in FIG. 5, clamped to another type of rail.
Figure 12:
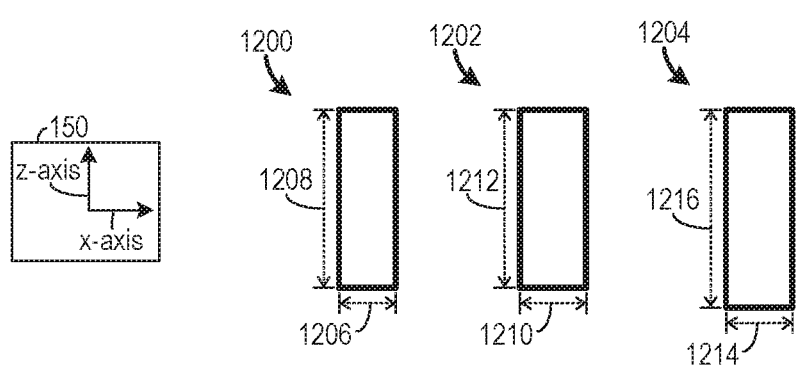
FIG. 12 is a use-case illustration of different rails to which clamping devices can be attached, according to an exemplary embodiment.

FIG. 1 shows different types of clamping devices in an exemplary operating environment. FIG. 2 shows a detailed view of one of the clamping devices, depicted in FIG. 1. FIG. 3 shows a detailed view of another clamping device, depicted in FIG. 1. FIGS. 4 and 5 show an illustration of an exemplary clamping device in different height configurations. FIG. 6 shows an exploded view of the clamping device, depicted in FIG. 5. FIG. 7 shows a detailed view of a spacer included in the clamping device, shown in FIG. 6. FIGS. 8-10 show a clamping sequence for the clamping device, illustrated in FIG. 6. FIG. 11 shows the clamping device attached to a differently dimensioned rail. FIG. 12 shows rails of different dimensions to which clamping devices can be attached, in a use-case example.

FIG. 1 shows an illustration of a system 100 including a clamping object 102 with clamping devices 104 coupled thereto. The clamping object 102 is a medical assembly (e.g., medical table assembly with a patient 106 thereon) including a rail 108, in the illustrated embodiment. However, the clamping devices 104 may be engaged with a table panning device, in other examples. In such an example, the table panning device may be designed as a user interface for panning a table. In other examples, the clamping devices may be configured to attach to a pole, such and an intravenous (IV) bag pole or other suitable objects such as workstands, industrial machines, furniture objects, etc.

The rail 108, in the illustrated embodiment, is positioned on a first lateral side 110 of the clamping object 102. However, the rail may be located in other positions, in other embodiments. Furthermore, it will be appreciated that additional rails may be included in the clamping object 102 allowing for additional accessory attachment, if wanted. To elaborate, another rail may be positioned on a second lateral side 128 of the clamping object 102 or in some embodiments, rails may traverse each side of the object.

The clamping devices 104 are designed to efficiently and robustly attach to the rail 108. The clamping devices 104 are also configured to attach to rails of varying height and thickness. Consequently, the applicability of the devices can be expanded. Various structural features allowing the aforementioned benefits to be achieved include knobs 112 axial translating pins toward/away from a side 114 (e.g., lateral side) of the rail 108 to facilitate clamping thickness adjustments. In this way, rails with varying thicknesses can be securely clamped by the device. Spacers 500, shown in FIGS. 5-6 and described in greater detail herein, enabling clamping height adjustability, may also be included in the clamping devices 104. In this way, the adaptability of the clamping devices may be further increased, if desired.

The clamping devices 104 may include a variety of accessories, accessory interfaces, etc. Specifically, a first clamping device 116 is depicted with an articulating arm 118 having a table 120 extending therefrom. The table 120 may have a planar top 121 surface allowing a user input device (e.g., mouse) to be manipulated thereon. A second clamping device 122 is also depicted with an articulating arm 124 having a display-mounting interface 126 extending therefrom. In this way, a display may be rotatably attached to the table. However, numerous suitable types of accessories coupled to or integrated into the clamping devices have been contemplated.

The clamping devices 104 are removably attached to the rail 108 and can be repositioned (e.g., slid) lengthwise (e.g., longitudinally) along the rail when placed in a disengaged configuration. As a result, the devices can be quickly and efficiently repositioned according to a user's predilection.

An axis system 150 is provided in FIG. 1 as well as FIGS. 2-12, for reference. The axis system 150 includes a z-axis, a y-axis, and an x-axis. The z-axis may be parallel to a gravitational axis, the y-axis may be a longitudinal axis, and/or the x-axis may be a lateral axis. However, the axes may have other orientations, in other examples.

One or more of the clamping devices 104 shown in FIG. 1 may also be coupled to a second rail 130, schematically illustrated in FIG. 1. The second rail 130 may have a different size than the first rail. In this way, a second rail having an upgraded or downgraded size can be attached to the first rail 108 to allow additional accessories to be mounted on the medical table. Consequently, the table can be further customized based on the operating environment, if wanted. Still further, in other examples, the rail 108 may be repositioned on the object to allow clamps to be applied to either of the lateral sides of the rail, further expanding rail clamping capabilities. For instance, in one use-case example, an anesthesia screen holder clamp may be attached to one side of the rail and a rear rail clamp may be attached to another side of the rail. In another use-case example, the strength of the attachment between the rail 108 and the clamping devices 104 may accommodate for tilting of the rail while the relative position of the device and the rail is substantially fixed.

FIG. 2 shows a detailed illustration of the clamping device 116, shown in FIG. 1. The articulating arm 118 and the table 120 are again depicted. The articulating arm 118 includes a first joint 200 (e.g., first hinge) and a second joint 202 (e.g., second hinge), in the illustrated example. In this way, the articulating arm 118 may rotate about two or more axes. Thus, the joints 200 and 202 in the articulating arm 118 enable the table's position to be adjusted based on user predilection. However, in other examples, the joints may be omitted from the arm or three or more joints may be integrated into the arm to allow for additional freedom of movement of the table. The joints 200 and 202 as well as the other joints described herein may include suitable components to facilitate rotation such as pins, sleeves, bearings, etc. The strength of the clamping device 116, may allow in some examples, the arm 118 to extend further away from the base clamping unit without disengaging or otherwise degrading the device. As a result, the accessory positioning capabilities of the device are further increased.

FIG. 3 shows a detailed illustration of the clamping device 122, shown in FIG. 1. The articulating arm 124 and the display-mounting interface 126 are again depicted. The display-mounting interface 126 may include mounting bosses 300 or other suitable attachment structures to enable a display to be attached thereto. The articulating arm 124 also includes a plurality of joints 302 (e.g., hinges), enabling the display to be oriented at different viewing angles. However, in other instances, the joints may be omitted from the arm or an alternate number of joints may be integrated into the articulating arm 124.

FIGS. 4 and 5 illustrate an exemplary clamping device 400. It will be appreciated that the clamping device 400 shown in FIGS. 4 and 5 is an example of one of the clamping devices 104 depicted in FIGS. 1-3. As such, the clamping device 400 may share common structural and/or functional features with one or more of the clamping devices 104, shown in FIGS. 1-3, or vice versa.

The clamping device 400 includes a clamping jaw 402 with a first clamping arm 404 (e.g., a lower clamping arm). The clamping jaw 402 is designed to pivot to allow the device to be efficiently clamped and unclamped. A lever 600, shown in FIG. 6, enables the clamping jaw 402 to be manually pivoted. However, motorized pivoting of the jaw may be used, in other examples.

The first clamping arm 404 includes a distal end 406 with a flange 408. The flange 408 is tapered, in the illustrated embodiment, and therefore may be referred to as a tapered section. Tapering the surface in this manner allows a rail or other object being clamped to be smoothly guided into a clamped arrangement in the clamping device 400. Specifically, in one use-case example, a user may forgo device lever actuation and simply push the tapered section against the rail to induce clamping arm opening. Consequently, clamping operation may unfold more efficiently and intuitively. However, in other examples, the flange may have a non-tapered shape and user may actuate the lever to disengage the clamp.

The clamping device 400 is also shown including a body 410 with an upper section 412 and a lower section 414. However, the device may be alternately partitioned, in other embodiments.

A second clamping arm 416 (e.g., upper clamping arm) is included in the upper section 412 of the body 410. The second clamping arm 416 includes a flange 418 configured to interface with a lateral side of a rail or other suitable clamping object. Thus, the upper and lower clamping arms vertically laterally delimit the clamping object. It will also be understood that the clamping arms also vertically delimit the rail, when engaged. Additionally, the second clamping arm 416 may remain substantially stationary with regard to the upper section 412.

The lower section 414 of the body 410 also includes lower surfaces 420 and rear surfaces 422 axially guiding the rail into a desired position when the clamping device transitions from the disengaged configuration to the engaged configuration. However, other profiles of the lower section 414 of the body have been contemplated, such as designs omitting one or more of the lower surfaces 420.

The clamping device 400 also includes a knob 424 with a pin 426 designed to axially translate toward/away from a lateral side of the rail opposing the side of the rail delimited by the flange 408. In this way, the clamping thickness of the device may be adjusted to allow rails of varying thicknesses to be securely clamped, thereby increasing device adaptability. Thus, the axially translating pin 426 may also provide an intuitive ancillary engagement feature in the device, the first engagement feature being the clamping accomplished by the first clamping arm 404 and the second clamping arm 416. Furthermore, engaging the pin 426 with the lateral side of the rail reduces play in the device when clamped.

Rotation of a gripping portion 428 of the knob 424 induces axially translation of the pin 426, in the illustrated example. To elaborate, a threaded section 427 of the pin 426, shown in FIG. 6, is designed to engage with a threaded section 429 of an opening 605 in the upper section 412 of the body 410. In other embodiments, axially translation of the pin 426 may be carried out through other suitable techniques such as axially pushing/pulling the knob inward/outward and locking the axial position of the knob via a radially aligned pin, for instance. Rotating or pushing/pulling the knob may be performed by a user, in one example. In one particular example, the knob 424 and/or the lever 600, shown in FIG. 6, may be designed to be actuated by a user using one hand, if desired. The strength of the spring in the spring loaded plungers 620, shown in FIG. 6, and/or the knob's diameter 650, shown in FIG. 6, and/or contour may be selected to allow one-hand actuation to be carried out. However, it will be understood that two-hand actuation of the knob and/or lever may also be used, in some embodiments. Still further in other embodiments, motorized means of knob actuation may be deployed.

The clamping device 400, shown in FIGS. 4-5, may also include attachment components 430 (e.g., mounting screws) attaching the upper section 412 to the lower section 414. The clamping device 400 may also include dowels 432 attaching to the upper section 412 of the body 410 and allowing accessories to be attached thereto. As shown in FIGS. 4-5, both the dowels 432 and the attachment components 430 are configured to extend through openings 434 in the upper section 412. However, other attachment configurations of the body may be used, in other examples.

FIGS. 4 and 5 show an example of a clamping device 400 in different height configurations. To allow for the height adjustment of the clamping device 400, spacers 500 shown in FIG. 5, are placed between the upper section 412 and the lower section 414 of the body 410. The attachment components 430 may extend through openings in the spacers 500 to allow for spacer integration. The spacers 500 may be positioned on a shelf 501 of the lower section 414 of the body 410, in the illustrated example. The shelf allows the spacer to be retained in a desired location, in some examples. However, other contours of the upper section of the body may be used, in other examples.

FIG. 6 shows an exploded view of the clamping device 400 illustrated in FIG. 5. The body 410 including the upper section 412 and lower section 414 is again depicted along with the knob 424, clamping jaw 402, attachment components 430, and dowels 432.

When assembled, the clamping jaw 402 may be position at least partially within a recess 602 in the lower section 414 of the body 410. In this way, a more compact device arrangement can be achieved, if wanted. Specifically in one example, interior surfaces 415 of the lower section 414 bound sides 417 of the clamping jaw 402. Delimiting the jaw in this manner also may enable the jaw to be maintained in a desired position which enables jaw rotating during clamping/unclamping action in the device. However, alternate profiles of the body and the jaw have been contemplated, such as lower sections of the body without sidewalls.

Routing the knob pin 426 through the upper section 412 of the body 410 also enables device compactness to be further increased, if desired. To elaborate, the pin 426 traverses a portion 603 of the upper section 412 vertically above the clamping jaw 402. An opening 605 in the upper section 412 allows the pin to be inserted therethrough. Positioning the pin vertically above the jaw prevents the pin from interfering with jaw actuation. Increasing device compactness may also enable the device's weight to be reduced, if desired, in some examples. Reducing the device's weight allows users to more easily transport and otherwise manipulate the clamping device 400. Specifically, in one example, the device may weight approximately 0.5 kilograms (kg) or less. However, other device weights and/or profiles have been envisioned. For instance, the device may weigh more than 0.5 kg. Providing a device with a compact arrangement may also allow the device to be easily cleaned. It will also be appreciated that the size of the clamping device may also allow a drape (e.g., sterile drape) to at least partially enclose the device, in certain embodiments. Consequently, the device's capabilities are further expanded.

The clamping device 400 may further include a hinge 604 (e.g., hinge pin) and/or a screw 606 (e.g., set screw). When the device is assembled, the hinge 604 mates with openings 607 in the lower section 414 of the body 410 and an opening 608 in the clamping jaw 402. The screw 606 may allow the hinge 604 to be retained in a desired location in the device.

The pin 426 in the knob 424 is again illustrated. The pin 426 may include a recess 610 mating with a knob screw 612. In this way, axial translation of the pin 426 can be delimited. However, the knob screw 612 may be omitted from the device, in other embodiments. However, other techniques for delimiting the movement of the knob pin have been contemplated.

The clamping device 400 may further include guide rods 614 mating with opening 616 in the spacers 500. The guide rods 614 may also mate with openings 618 in the lower section 414 of the body 410. Furthermore, the guide rods 614 may be configured to attach (e.g., threadingly engage) with attachment components 430. In this way, the upper and lower section of the body may be removably coupled to one another.

Spring loaded plungers 620 may be positioned in the lower section 414 of the body 410, when the device is assembled. The spring loaded plungers 620 are designed to exert a return force on the first clamping arm 404 of the clamping jaw 402 when the device is in the disengaged configuration. The spring loaded plungers 620 include an outer housing 522 enclosing a spring and a moveable component 524 (e.g., adjustable cylinder).

The clamping device 400 may also be configured to generate acoustic and/or haptic feedback, providing cues to the user of engagement and disengagement of the device. For instance, the interaction between the spring loaded plungers 620 and the first clamping arm 404 may provide the acoustic and/or haptic feedback. In this way, the device may be efficiently and more confidently clamped and unclamped from selected objects.

The lever 600 of the clamping jaw 402 allowing for jaw actuation is also shown in FIG. 6. The lever 600 is shown extending downward away from the first clamping arm 404. However, other lever arrangement may be utilized, in other examples.

The flange 408 at the distal end 406 of the first clamping arm 404 is also illustrated in FIG. 6. The clamping jaw 402 includes a section 626 at a proximal end 628 with the opening 608. A curved surface 609 of the jaw 402 is also shown in FIG. 6. The curved surface 609 may facilitate rotation of the jaw during device engagement/disengagement. However, other jaw profiles may be used, in other examples.

A plurality of accessory mounting components 630 (e.g., screws) configured to attach to accessories, may also be included in the clamping device 400. However, in other examples, the accessory mounting components may be omitted from the device.

A variety of materials for clamping device construction have been contemplated such as polymeric materials (e.g., polyethylene), metal materials (e.g., steel, aluminum, etc.), ceramic materials, etc. Material characteristics such as strength to weight ratio, abrasion resistance, etc., as well as the device's expected operating environment may be taken into account when selecting materials for construction of the device. For example, certain components in the device may be constructed out of a polymer when decreased device weight is wanted. However, in one use-case example if structural integrity is favored, a portion of the components may be constructed out of steel or aluminum. However, numerous suitable material construction schemes have been contemplated.

FIG. 7 shows a detailed view of one of the spacers 500. The opening 616 in the spacer 500 is again shown. The spacer 500 includes sidewalls 700 as well as an upper surface 702 and a lower surface 704. The upper surface 702 may be in contact with the upper section 412 of the body 410 shown in FIG. 6. Conversely, the lower surface 704 may be in contact with the lower section 414 of the body 410, shown in FIG. 6.

FIGS. 8-10 show the clamping device 400 in different stages occurring during the transition from the unclamped configuration to the clamped configuration. FIG. 8 specifically shows the clamping device 400 partially mated with a rail 800. To elaborate, an upper side 802 of the rail 800 interacts with the second clamping arm 416 (e.g., upper clamping arm) in the upper section 412 of the body 410.

The clamping jaw 402 pivots about an axis of rotation 804. As previously discussed, the hinge 604, shown in FIG. 6, allows for jaw rotation. To place the clamping jaw 402 in the unclamped configuration the lever 600 is pushed in direction 806 to rotate the jaw 402 in direction 808 moving the first clamping arm 404 (e.g., lower clamping arm) away from the second clamping arm 416 (e.g., upper clamping arm). In this way, the clamp can be opened to initiate rail engagement.

As shown in FIG. 8, the lower surfaces 420 of the lower section 414 of the body 410 guide a lower side 810 of the rail into the clamping device. Viewing plane A-A' indicating the cross-section of the views shown in FIGS. 9-11, is also indicated in FIG. 8.

FIG. 9 shows the clamping device 400 in cross-section to reveal interior components. The clamping jaw 402 is again shown pivoting about the hinge 604. The rail 800 is also shown interacting with the second clamping arm 416 (e.g., upper clamping arm). As depicted, the flange 408 of the first clamping arm 404 (e.g., lower clamping arm) is spaced away from the rail 800 allowing for insertion of the rail into the device. One of the spring loaded plungers 620 is shown in FIG. 9. The plunger may exert a return force on the first clamping arm 404 (e.g., surface on a proximal side of the arm) when the lever 600 is urged into the disengaged position. In this way, the lever may return to its engaged position subsequent to release of the lever.

The knob 424 with the pin 426 are additionally illustrated in FIG. 9. The knob screw 612 is shown mated with the recess 610 to delimit axial movement of the pin 426. Consequently, the knob 424 may be inhibited from inadvertently being decoupled from the body 410. The pin 426 is also shown axially retracted away from the rail 800 allowing the rail to mate with the clamping device. However, in other examples, the pin may be positioned axially closer to the rail when the device is transitioned from a disengaged state to an engaged state.

The clamping device 400 may be slid lengthwise (i.e., into and out of the page in the frame of reference in FIG. 9) along the rail 800. In this way, the device can be repositioned and/or clamped in a number of different rail locations, as desired.

FIG. 10 shows the clamping device 400 placed in an engaged configuration. In the engaged configuration the second clamping arm 416 interfaces with the upper side 802 of the rail 800 and the first clamping arm 404 interfaces with the lower side 810 of the rail. Additionally in the engaged configuration, the knob pin 426 interfaces with a lateral side 1000 of the rail 800. The opposing lateral side 1001 interfaces with portions (e.g., lips) of the first clamping arm 404 and the second clamping arm 416. In this way, the rail 800 may be securely clamped laterally and vertically. Consequently, when in the engaged configuration the clamping device 400 can efficiently manage bidirectional vertical loading, torsional loading, and bending moment load. Therefore, the chance of the device becoming inadvertently disengaged due to external loading is significantly reduced. For instance, forces acting upward or downward on the table 120, shown in FIG. 2 and indicated at 134 and 132, transferred to the clamping device 400 shown in FIG. 10 may not cause device disengagement.

FIG. 10 also shows the flange 408 in a location that is not vertically above the axis of rotation 804 of the clamping jaw 402. Specifically, a tip 1002 of the flange 408 is vertically aligned with the axis of rotation 804, in the depicted embodiment. Arranging the tip 1002 of the first clamping arm 404 in this manner reduces the chance of the device becoming unintentionally disengaged from the rail. In this way, robust engagement between the clamping device 400 and rail 800 can be achieved. However, other positions of the flange 408 with regard to the axis of rotation have been envisioned, such as lower positions.

FIG. 11 shows the clamping device 400 engaged with a differently sized rail 1100. To elaborate, the rail 1100 has a different thickness than the rail 800, shown in FIG. 10. To accommodate for the variation in thickness, the knob 424 is adjusted to axial translate the pin 426 into a position interfacing with (e.g., in face sharing contact with) the lateral side 1102 of the rail 1100. Consequently, the device can be adapted to securely clamp rails of different thicknesses.

FIG. 12 shows a first rail 1200, a second rail 1202, and a third rail 1204 of varying dimensions. The clamping device 400, shown in FIGS. 4-11, may be configured to engage with any of these rails due to the device's clamping thickness and height adjustability. The thickness adjustability is achieved via the adjustable knob and the height adjustability is achieved via the removable spacers positioned between sections of the body of the device, as previously discussed.

The dimensions of the first rail 1200 may be 7.7 millimeters (mm) in thickness and 25 mm in height. The thickness of the first rail is indicated at 1206 and the height of the first rail is indicated at 1208. The dimensions of the second rail 1202 may be 10 mm in thickness and 25 mm in height. The thickness of the second rail is indicated at 1210 and the height of the second rail is indicated at 1212. Additionally, the dimensions of the third rail 1204 may be 9.6 mm in thickness and 28.7 mm in height. The thickness of the third rail is indicated at 1214 and the height of the third rail is indicated at 1216. It will be appreciated that the abovementioned rails sizes may be frequently used in the healthcare industry. As such, in one use-case example, the clamping device 400, shown in FIGS. 4-11 may be configured to clamp rails with 5 mm-10 mm thicknesses and/or 25 mm-30 mm heights. Thus, designing the clamping device that can dimensionally adjust to accommodate engagement with these different rails sizes allows the device to be used in a wide variety of practical scenarios. Consequently, the applicability of the device may be increased. However, the clamping device may be designed to clamp to rails with thicknesses and/or heights in a variety of ranges.

A technical effect of using a clamping device with upper and lower clamping arms selectively coupling upper and lower sides of a rail and a knob with a pin axial extending and retracting to engage/disengage with a lateral side of the rail is to provide a strong connection between the device and rail to react a variety of types of loading (e.g., bidirectional vertical loads, torsional loads, bending moment load, and the like) to reduce the likelihood of unexpected device/rail disengagement during use. Another technical effect providing a clamping device with the abovementioned features is to allow rails of varying dimensions (e.g., thickness and/or height) to be clamped by the device. Consequently, the adaptability of the device is increased.

In another representation, a medical clamping device is provided that comprises a lower clamping arm rotatable with regard to an upper clamping arm to engage and disengage upper and lower sides of a rail on a lateral side of table and a pin interposed between the upper and lower clamping arms and configured to axially translate toward and away from a lateral side of the rail.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features. As described herein "approximately" and "substantially" refer to values of within plus or minus five percent, unless otherwise noted.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A clamping device configured to be attached to a clamping object, the clamping device comprising:
    a body including an upper section and a lower section, the lower section of the body removable from the upper section of the body, the lower section of the body having a first wall and a second wall, the upper section of the body having a clamping arm configured to interface with a first side of the clamping object;
    a hinge pin extending through the lower section of the body;
    a clamping jaw positioned between the first and second walls of the lower section of the body, the clamping jaw configured to pivot about the hinge pin, and the clamping jaw including a clamping arm configured to interface with a second side of the clamping object opposite the first side of the clamping object;
    a spacer positioned between the upper section of the body and the lower section of the body, and the spacer configured to be removed to adjust a vertical distance between the clamping arm of the upper section of the body and the clamping arm of the clamping jaw;
    a guide rod received by an opening formed into the first wall of the lower section of the body, and the guide rod mating with an opening of the spacer; and
    a knob including a pin, and the pin configured to axially translate through an opening in the upper section of the body toward a third side of the clamping object extending between the first and second sides of the clamping object to contact the third side of the clamping object and translate away from the third side of the clamping object in response to a rotation of the knob.

2. The clamping device of claim 1, in combination with the clamping object, wherein the clamping object is a rail in a medical assembly, wherein the rail is arranged either in a horizontal position or a tilted position.

3. The clamping device of claim 1, wherein the guide rod engages with an attachment component that extends through the upper section of the body.

4. The clamping device of claim 1, wherein the clamping arm of the clamping jaw includes a tapered section at a distal end.

5. The clamping device of claim 1, wherein the guide rod extends in a direction that is substantially perpendicular to an axis of rotation of the clamping jaw.

6. The clamping device of claim 1, wherein the clamping arm of the clamping jaw includes a flange configured to contact a fourth side of the clamping object opposite the third side of the clamping object, and wherein a tip of the flange of the clamping arm of the clamping jaw does not vertically extend above an axis of rotation of the clamping jaw.

7. The clamping device of claim 6, wherein the tip of the flange of the clamping arm of the clamping jaw is parallel to the axis of rotation of the clamping jaw.

8. The clamping device of claim 1, wherein the clamping jaw is positioned between an interior surface of the first wall of the lower section of the body and an interior surface of the second wall of the lower section of the body.

9. The clamping device of claim 1, in combination with an articulating arm, wherein the articulating arm is configured to be attached to the clamping device, and wherein the articulating arm is rotatable about two or more axes.

10. A medical accessory clamping device configured to be attached to one or more rails, the medical accessory clamping device comprising:
- a body including an upper section and a lower section, the lower section of the body removable from the upper section of the body, the lower section of the body having a first wall and a second wall, and the upper section of the body having a clamping arm configured to interface with a first side of the one or more rails;
- a hinge pin extending through the lower section of the body;
- a clamping jaw positioned between the first and second walls of the lower section of the body, the clamping jaw configured to pivot about the hinge pin, and the clamping jaw including a clamping arm configured to interface with the first side of the one or more rails;
- a spacer positioned between the upper section of the body and the lower section of the body, and the spacer configured to be removed to adjust a vertical distance between the clamping arm of the upper section of the body and the clamping arm of the clamping jaw;
- a guide rod received by an opening formed into the first wall of the lower section of the body, and the guide rod mating with an opening of the spacer; and
- a knob including a pin, and the pin configured to be inserted into an opening in the upper section of the body and axially translate through the opening in the upper section of the body to contact a second side of the one or more rails opposite the first side of the one or more rails and translate away from the second side of the one or more rails.

11. The medical accessory clamping device of claim 10, further comprising a spring loaded plunger positioned in the body and configured to exert a return force on the clamping jaw when the clamping jaw is rotated away from a clamping position.

12. The medical accessory clamping device of claim 10, wherein the guide rod is a first guide rod, wherein the medical accessory clamping device further comprises a second guide rod received by an opening formed into the second wall of the lower section of the body, and wherein the first guide rod and the second guide rod extend in a direction substantially perpendicular to an axis of rotation of the clamping jaw.

13. The medical accessory clamping device of claim 10, wherein the clamping arm of the clamping jaw includes a tapered section configured to extend vertically along the first side of the one or more rails.

14. The medical accessory clamping device of claim 10, wherein the spacer is one of a plurality of removable spacers positioned between the upper section of the body and the lower section of the body.

15. The medical accessory clamping device of claim 10, in combination with the one or more rails, wherein the one or more rails include a first rail and a second rail, wherein the medical accessory clamping device is configured to be removably attached to the first rail and the second rail, and wherein the second rail is different in size from the first rail.

16. The medical accessory clamping device of claim 10, wherein the medical accessory clamping device is configured to be repositioned along a length of the one or more rails without being removed from the one or more rails.

17. The medical accessory clamping device of claim 10, in combination with a support assembly, wherein the support assembly includes an articulating arm and a support structure coupled to the articulating arm, and wherein the support structure is a table or a display-mounting interface.

18. A medical accessory clamping device configured to be attached to a rail, the medical accessory clamping device comprising:
- a body including an upper section and a lower section, the lower section of the body removable from the upper section of the body, the lower section of the body having a first wall and a second wall, and the upper section of the body having an upper clamping arm configured to interface with an upper side of the rail;
- a hinge pin extending through the lower section of the body;
- a clamping jaw positioned between the first and second walls of the lower section of the body, the clamping jaw configured to pivot about the hinge pin, and the clamping jaw including a lower clamping arm configured to interface with a lower side of the rail;
- a spacer positioned between the upper section of the body and the lower section of the body, and the spacer configured to be removed to adjust a vertical distance between the upper clamping arm of the upper section of the body and the lower clamping arm of the clamping jaw;
- a guide rod received by an opening formed into the first wall of the lower section of the body, and the guide rod mating with an opening of the spacer; and
- a knob including a pin, the pin extending through the upper section of the body, and the pin configured to axially translate through a hole in the body to contact a first lateral side of the rail and translate away from the first lateral side of the rail in response to a rotation of the knob.

19. The medical accessory clamping device of claim 18, wherein the spacer is one of a plurality of removable spacers positioned between the upper section of the body and the lower section of the body.

20. The medical accessory clamping device of claim 19, wherein the lower clamping arm of the clamping jaw includes a tapered section at a distal end, wherein the tapered section of the lower clamping arm of the clamping jaw includes a tip configured to extend vertically along a second lateral side of the rail opposite the first lateral side of the rail, and wherein the lower clamping arm of the clamping jaw is positioned between a lower surface of the first wall of the lower section of the body and a lower surface of the second wall of the lower section of the body.

* * * * *